(12) United States Patent
Sellers et al.

(10) Patent No.: US 8,980,590 B2
(45) Date of Patent: Mar. 17, 2015

(54) PROCESS FOR SEPARATION OF RENEWABLE MATERIALS FROM MICROORGANISMS

(71) Applicant: BP Biofuels UK Limited, Naperville, IL (US)

(72) Inventors: Martin J. Sellers, Wokingham (GB); David Jeffers, Woking Surrey (GB); Jean-Charles Dumenil, Little Chalfont (GB); Vidya Pai, Rockville, MD (US); Jacob Borden, San Diego, CA (US)

( * ) Notice: Subject to any disclaimer, the term of this patent is extended or adjusted under 35 U.S.C. 154(b) by 0 days.

(21) Appl. No.: 13/930,309

(22) Filed: Jun. 28, 2013

(65) Prior Publication Data

US 2014/0004579 A1    Jan. 2, 2014

Related U.S. Application Data

(60) Provisional application No. 61/666,096, filed on Jun. 29, 2012.

(51) Int. Cl.
    *C12P 7/64* (2006.01)

(52) U.S. Cl.
    USPC .................. 435/134; 435/255.1; 554/175

(58) Field of Classification Search
    USPC ................ 435/134, 255.1; 554/175
    See application file for complete search history.

(56) References Cited

U.S. PATENT DOCUMENTS

| | | | |
|---|---|---|---|
| 4,720,456 A | 1/1988 | Wagner et al. | |
| 5,179,012 A | 1/1993 | Gudin et al. | |
| 6,750,048 B2 | 6/2004 | Ruecker et al. | |
| 7,351,558 B2 | 4/2008 | Ruecker et al. | |
| 7,662,598 B2 | 2/2010 | Ruecker et al. | |
| 2011/0086386 A1 | 4/2011 | Czartoski et al. | |
| 2011/0295028 A1 | 12/2011 | Cherinko et al. | |
| 2012/0119862 A1* | 5/2012 | Franklin et al. | ........... 336/58 |

FOREIGN PATENT DOCUMENTS

| | | |
|---|---|---|
| EP | 1252324 A1 | 10/2002 |
| KR | 10-995575 B1 | 11/2010 |
| WO | WO 01/53512 A1 | 7/2001 |
| WO | WO 2011/059745 | 5/2011 |
| WO | WO 2011/133181 | 10/2011 |
| WO | WO 2011/153246 A2 | 12/2011 |
| WO | WO 2012/061647 A2 | 5/2012 |

OTHER PUBLICATIONS

Jin, G. et al. Enzyme Assisted Extraction of Lipids Directly from the Culture of the Oleaginous Yeast *R. toruloides*. Bioresource Technology 111:378-382, Feb. 6, 2012.*

Papanikolaou et al. "Lipids of oleaginous yeasts. Part II: Technology and potential applications", vol. 113, No. 8, Aug. 15, 2011, pp. 1052-1073.

Zhang et al. "Mechanism of lipid extraction from *Biotryocccus braunii* FACHB 357 in the biphasic bioreactor", Science Direct, vol. 154 Issue 4, Jul. 20, 2011 pp. 281-284.

Zhang et al. "Screening of biocompatible organic solvents for enhancement of lipid milking from *Nannochloripsis* sp." Science Direct vol. 46, Issue 10, Oct. 2011, pp. 1934-1941.

Pena et al. Rehydration temperature is critical for metabolic competence and for membrane integrity in active dry yeast (ADY), Arch Microbiolo, 1992 pp. 75-80.

* cited by examiner

*Primary Examiner* — Ralph Gitomer

(57) ABSTRACT

Methods of separating renewable materials, such as lipids, from microorganisms, such as oleaginous yeasts, may include conditioning cell walls of the microorganisms to form, open or enlarge pores, and removing at least a portion of the renewable material through the pores. These methods may result in delipidated microorganisms with cell walls that are substantially intact and with mesopores. These delipidated microorganisms may be used to produce biofuels.

11 Claims, 1 Drawing Sheet

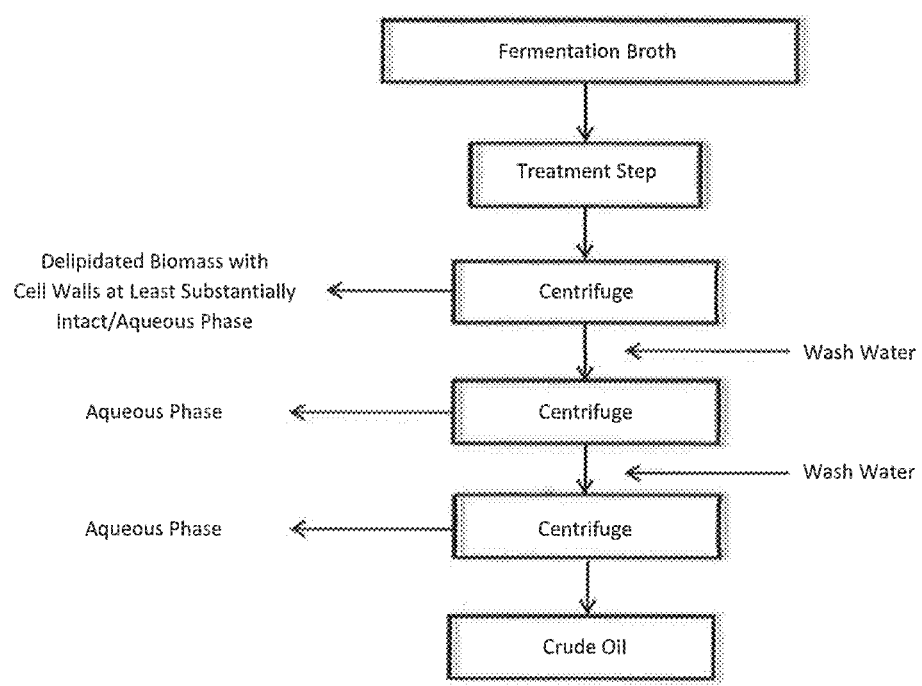

PROCESS FOR SEPARATION OF RENEWABLE MATERIALS FROM MICROORGANISMS

CROSS-REFERENCE TO RELATED APPLICATION

This application claims the benefit of prior U.S. Provisional Application No, 61/666,096, filed Jun. 29, 2012, which is hereby incorporated by reference in its entirety.

NAMES OF THE PARTIES TO A JOINT RESEARCH AGREEMENT

For purposes of 35 U.S.C. §103(c)(2), a joint research agreement was executed between BP Biofuels UK Limited and Martek Biosciences Corporation on Dec. 18, 2008 in the field of renewable materials. Also for the purposes of 35 U.S.C. §103(c)(2), a joint development agreement was executed between BP Biofuels UK Limited and Martek Biosciences Corporation on Aug. 7, 2009 in the field of renewable materials.

TECHNICAL FIELD

The invention relates to methods and systems directed to renewable materials and biofuels production. Aspects of the invention relate to extracting renewable materials from oleaginous microorganisms.

BACKGROUND

Issues of greenhouse gas levels and climate change have led to development of technologies seeking to utilize natural cycles between fixed carbon and liberated carbon dioxide. As these technologies advance, various techniques to convert feedstocks into biofuels have been developed. However, even with the above advances in technology, there remains a need and a desire to improve economic viability for conversion of renewable carbon sources to fuels.

Vegetable oil derived biodiesel fuel may have benefits, such as being renewable, biodegradable, nontoxic, and containing neither sulfur nor aromatics versus conventional petroleum (fossil) diesel. But, one potential disadvantage of vegetable oil derived biodiesel is high cost, most of which is due to the cost of the vegetable oil feedstock. Therefore, the economic aspect of biodiesel fuel production has been at least somewhat limited by the cost of the vegetable oil raw materials.

Lipids for use in nutritional products can be produced in algae. Manufacturing a lipid in algae may include growing the algae, drying it, and extracting the intracellular lipids from it. Extracting material from within the algae can be difficult.

There is a need and a desire for methods and systems for extracting renewable materials from oleaginous microorganisms that result in a high yield of material extracted and minimal disruption of the cell wall structures.

SUMMARY

The invention relates to methods and systems for extracting renewable materials from oleaginous microorganisms, as well as delipidated microorganisms resulting from such methods.

According to certain embodiments, a process for separating renewable materials from microorganisms containing the renewable materials may include conditioning cell walls of the microorganisms to form, open or enlarge pores, and removing at least a portion of the renewable material through the pores. In order to form, open or enlarge the pores of the cell walls, the process may include denaturing the cell wall structures and/or cell wall components. The cell wall structures and/or cell wall components may include transport proteins, integral membrane proteins, receptor proteins, agglutination proteins, antigenic proteins, septum, bud scars, decorating carbohydrates, non-structural carbohydrates, structural carbohydrates, glucans, mannans, mannoproteins, acetylglucosamine, chitin, dolipores, pore caps, protein cross-links, carbohydrate cross-links, protein-carbohydrate cross-links, embedded lipids, phospholipids, glycerides, sterols, sterol esters, or any combination thereof.

According to certain embodiments, the cell wall or cell wall structure remains at least substantially intact.

The renewable material may include biofuels biofuel precursors. For example, the biofuels or biofuel precursors may include lipids, organic acids, amino acids, alcohols, esters, alkanes, alkenes, olefins, paraffins, waxes, or combinations thereof. According to certain embodiments, the biofuels or biofuel precursors may include substantially polar materials, while in other embodiments the biofuels or biofuel precursors may include substantially non-polar materials. According to certain embodiments, a partition, phase, or layer may separate polar renewable materials from non-polar renewable materials. According to certain embodiments, the renewable material includes lipids and/or triglycerides.

According to certain embodiments, the renewable material can be manufactured into a food product, a pharmaceutical composition, a cosmetic product, and/or an industrial composition. Examples of food products into which the renewable material can be manufactured include: human foods, animal foods, medical foods, food additives, beverages, therapeutic drinks, nutritional drinks, functional foods, supplements, nutraceuticals, infant formulas, foods for pregnant or nursing women, and geriatric foods.

The microorganisms used herein may include algae, fungi, and/or bacteria. In particular, the fungi may include oleaginous yeast. According to certain embodiments, the oleaginous yeast may belong to the genus *Rhodotorula, Pseudozyma,* or *Sporidiobolus*. In particular, the yeast may be *Sporidiobolus pararoseus* or *Rhodotorula ingeniosa*. For example, the microorganism may correspond to one or more of ATCC Deposit No. PTA-12508 (Strain MK29404 (Dry1-13J)), ATCC Deposit No. PTA-12509 (Strain MK29404 (Dry1-182J)), ATCC Deposit No. PTA-12510 (Strain MK29404 (Dry1-173N)), ATCC Deposit No. PTA-12511 (Strain MK29404 (Dry55)), ATCC Deposit No. PTA-12512 (Strain MK29404 (Dry41)), ATCC Deposit No. PTA-12513 (Strain MK29404 (Dry1)), ATCC Deposit No. PTA-12515 (Strain MK29404 (Dry1-147D)), or ATCC Deposit No. PTA-12516 (Strain MK29404 (Dry1-72D)). As another example, the microorganism may correspond to one or more of ATCC Deposit No. PTA-12506 (Strain MK29794 (KDry16-1)), ATCC Deposit No. PTA-12507 (Strain MK29794 (KDry7)), ATCC Deposit No. PTA-12514 (Strain MK29794 (K200 Dry1)), ATCC Deposit No. PTA-12517 (Strain MK29794 (33 Dry1)). Each of these deposits was deposited at American Type Culture Collection (ATCC®) 10801 University Boulevard, Manassas, Va. 20110-2209 on Feb. 9, 2012. Each of these deposits is commercially available.

Various techniques of conditioning the cell walls of the microorganism may include a thermal treatment, a chemical treatment, an enzymatic treatment, and/or a mechanical treatment.

The treatment process may be for any suitable duration or time, such as at least about 10 minutes, at least about 20 minutes, at least about 60 minutes, at least about 120 minutes, about 10 minutes to about 240 minutes, about 10 minutes to about 15 minutes, about 20 minutes to about 40 minutes, or about 30 minutes to about 180 minutes.

The treatment process may be at any suitable temperature, such as at least about 50 degrees Celsius, at least about 80 degrees Celsius, at least about 100 degrees Celsius, at least about 120 degrees Celsius, about 40 degrees Celsius to about 140 degrees Celsius, about 80 degrees Celsius to about 120 degrees Celsius, about 80 degrees Celsius, or about 100 degrees Celsius.

The treatment process may be at any suitable pressure, such as atmospheric pressure, full vacuum, partial vacuum, about 0.1 Bar to about 1,000 Bar, about 1 Bar to about 100 Bar, about 10 Bar to about 50 Bar, or about 0.1 Bar to about 0.5 Bar, each on an absolute pressure basis.

The treatment process may be at any suitable pH, such as about 1 to about 14, about 2 to about 14, about 2 to about 5, less than about 7, less than about 3, about 2, greater than about 9, or about 12.

According to certain embodiments, the conditioning may include a thermal treatment temperature of at least about 80 degrees Celsius. According to certain embodiments, the conditioning may include a duration of at least about 10 minutes. According to certain embodiments, the conditioning may include a thermal treatment at about 120 degrees Celsius for about 4 hours.

Removing at least a portion of the renewable material through the pores may be achieved using aqueous extraction techniques, solvent extraction techniques, mechanical extraction techniques, or any combination of these techniques. Mechanical extraction techniques may include extrusion, pressing, expelling, and/or the like. According to certain embodiments, the mechanical extraction may be carried out using a mechanical disruption device. The mechanical disruption device may include a homogenizer, a bead mill, a high-shear mixer, or any combination thereof. According to certain embodiments, the mechanical disruption device includes a bead mill.

According to certain embodiments, the solvent extraction technique may exclude the use of a mechanical disruption device.

According to certain embodiments, the microorganisms may include at least about 50 percent of renewable material on a weight basis before treatment and removal, and at least about 50 percent of the renewable material on a weight percent basis may pass through the pores while removing the renewable material from the microorganisms. The removal or separation of the renewable material from the microorganism may be at least about 50 percent, at least about 60 percent, at least about 80 percent, at least about 90 percent, at least about 95 percent, about 50 percent to about 99 percent, about 80 percent to about 95 percent, or about 90 percent to about 99 percent.

According to certain embodiments, the extraction yield of conditioned microorganisms may improve over unconditioned microorganisms, such as by at least about 10 percent, at least about 20 percent, at least about 30 percent, at least about 40 percent, at least about 50 percent, about 20 percent to about 40 percent, about 40 percent to about 50 percent over unconditioned microorganisms.

According to certain embodiments, the extraction yield of conditioned microorganisms may be at least about 50 percent, at least about 60 percent, at least about 70 percent, at least about 80 percent, at least about 90 percent, at least about 95 percent, about 50 percent to about 99 percent, about 80 percent to about 95 percent following conditioning and removal.

According to certain embodiments, the oil extractability index may increase by at least about 10 percent, at least about 20 percent, at least about 30 percent, at least about 40 percent, at least about 50 percent, about 20 percent to about 40 percent, about 40 percent to about 50 percent over unconditioned microorganisms, each on a weight basis.

According to certain embodiments, the oil extractability index may be at least about 50 percent, at least about 60 percent, at least about 70 percent, at least about 80 percent, at least about 90 percent, at least about 95 percent, about 50 percent to about 99 percent, about 80 percent to about 95 percent following conditioning and removal.

According to certain embodiments, the oil recovery index may increase by at least about 10 percent, at least about 20 percent, at least about 30 percent, at least about 40 percent, at least about 50 percent, about 20 percent to about 40 percent, about 40 percent to about 50 percent over unconditioned microorganisms, each on a weight basis.

According to certain embodiments, the oil recovery index may be at least about 50 percent, at least about 60 percent, at least about 70 percent, at least about 80 percent, at least about 90 percent, at least about 95 percent, about 50 percent to about 99 percent, about 80 percent to about 95 percent following conditioning and removal.

According to certain embodiments, the oil extraction yield index may increase by at least about 10 percent, at least about 20 percent, at least about 30 percent, at least about 40 percent, at least about 50 percent, about 20 percent to about 40 percent, about 40 percent to about 50 percent over unconditioned microorganisms, each on a weight basis.

According to certain embodiments, the oil extraction yield index may be at least about 50 percent, at least about 60 percent, at least about 70 percent, at least about 80 percent, at least about 90 percent, at least about 95 percent, about 50 percent to about 99 percent, about 80 percent to about 95 percent following conditioning and removal.

According to certain embodiments, the step of conditioning the cell walls of the microorganism may form pores comprising mesopores and/or micropores. In particular, at least about 50 percent, at least about 60 percent, at least about 70 percent, at least about 80 percent, at least about 90 percent, about 50 to about 90 percent, about 60 to about 80 percent, or about 85 percent of the total pores comprise mesopores (as measured as zeolite surface area) after conditioning, on a number basis.

Conditioned microorganisms may be produced according to any of the methods described herein. According to certain embodiments, the conditioned microorganisms may have a ratio of zeolite surface area: matrix surface area of greater than about 8, whereas a ratio of the zeolite surface area: matrix surface area of unconditioned microorganisms may be about 2. According to certain embodiments, the conditioned microorganisms have a zeolite surface area: matrix surface area of about 10, about 20, about 100, about 6 to about 100, about 8 to about 20, or about 10 to about 12. According to certain embodiments, the unconditioned microorganisms have a zeolite surface area: matrix surface area of about 4, about 3, about 1 about 1 to about 4, about 1.5 to about 3, or about 2 to about 2.5. Where the zeolite surface area and matrix surface area have been measured using analytical techniques from heterogeneous catalysis measurements.

Depleted, or delipidated, microorganisms may be produced according to any of the methods described herein. According to certain embodiments, during these methods, the cell walls of the delipidated microorganisms may remain at least substantially intact. More particularly, at least about 10 percent, at least about 20 percent, at least about 30 percent, at least about 40 percent, at least about 50 percent, at least about 60 percent, at least about 70 percent, at least about 80 percent, at least about 90 percent, at least about 95 percent, about 10 percent to about 99 percent, about 40 percent to about 90 percent, or about 70 percent to about 90 percent of the cell walls may remain at least substantially intact, on a number basis.

According to certain embodiments, cell wall pores means holes, openings, or apertures in the cell wall structure through the complete cell wall structure, such that substances may be transported across the cell wall structure via the pore.

According to certain embodiments, substantially intact refers to at least about 50 percent, at least about 60 percent, at least about 70 percent, at least about 80 percent, about 50 percent to about 80 percent, about 50 percent to about 60 percent, about 60 percent of the cell wall structure maintains structural integrity.

Renewable materials may be produced according to any of the methods described herein.

According to certain embodiments, a process for extracting lipids from oleaginous yeasts may include conditioning oleaginous yeast using a thermal treatment to increase cell wall porosity, and removing lipids from the oleaginous yeast with cell walls remaining at least substantially intact or alternatively completely intact.

Various techniques may be used to remove the lipids from the oleaginous yeast, such as solvent extraction or mechanical treatment.

According to certain embodiments, the oleaginous yeast may include at least about 50 weight percent lipids before extraction. Furthermore, when removing the lipids from the oleaginous yeast, at least about 50 weight percent of the lipids may be removed from the oleaginous yeast.

According to certain embodiments, conditioning the oleaginous yeast may include forming pores comprising mesopores and micropores. For example, at least about 50 percent, at least about 60 percent, at least about 70 percent, at least about 80 percent, or at least about 90 percent of the total pores formed may be mesopores (as measured by zeolite surface area), on a number basis.

According to certain embodiments, the oleaginous yeast may include a zeolite surface area:matrix surface area ratio of about 2 before conditioning, and a zeolite surface area:matrix surface area ratio of about 8 after conditioning.

The thermal treatment used to condition the oleaginous yeast may include temperatures above about 80 degrees Celsius, times greater than about 10 minutes, and a pH range of about 2 to about 14, for example.

The mechanical treatment used to remove the lipids from the oleaginous yeast may include using a homogenizer, a bead-mill, a high shear mixer, a press, an extruder, pressure disruption, wet milling, cryogenic milling, and/or dry milling, for example.

Biofuels may be produced using any of the methods described herein.

According to certain embodiments, a delipidated yeast may have cell walls that are substantially intact and with mesopores therein.

According to certain embodiments, the delipidated yeast may have less than about 20 weight percent of lipids remaining in the cell. According to certain embodiments, the delipidated yeast may have about 10 to about 30 weight percent of lipids remaining in the cell after removal versus the total lipid content of the unconditioned cell.

According to certain embodiments, at least about 10 percent, at least about 20 percent, at least about 30 percent, at least about 40 percent, at least about 50 percent, at least about 60 percent, at least about 70 percent, at least about 80 percent, at least about 90 percent, or at least about 95 percent of the cell walls may be substantially intact. According to certain embodiments, the delipidated yeast may have about 40 to about 80 percent of the cell walls substantially intact.

According to certain embodiments, the delipidated yeast may have a final mesopore content of at least about 10 percent, at least about 20 percent, at least about 30 percent, at least about 40 percent, at least about 50 percent, at least about 60 percent, at least about 70 percent, at least about 80 percent, or at least about 90 percent of the total pores on a number basis. According to certain embodiments, the delipidated yeast may have a final mesopore content of about 50 percent to about 90 percent of the total pores.

According to certain embodiments, a mixture for the production of biofuels may include delipidated oleaginous microorganisms with cell walls substantially intact, and lipid material.

According to certain embodiments, a manufacturing facility for the production of biofuels may include a lipid accumulation unit, and a lipid extraction unit in fluid communication with the lipid accumulation unit, wherein the lipid extraction unit comprises a cell conditioning device and a lipid separation device. The cell conditioning device may include one or more pieces of heat transfer equipment (such as heat exchangers), and the lipid separation device may include one or more pieces of extraction equipment. According to certain embodiments, the extraction equipment may include a mechanical disruption device.

According to certain embodiments, a process for producing biofuels may include: culturing yeast on a sugar solution to accumulate lipids within cell walls of the yeast; conditioning the yeast to form or enlarge pores in the cell walls; removing the lipids through the pores in the cell walls; separating the lipids from the yeast; and converting the lipids into a biofuel, such as by hydrotreating or transesterification.

BRIEF DESCRIPTION OF THE DRAWINGS

The accompanying drawing, which is incorporated in and constitutes a part of this specification, illustrates an embodiment of the invention and, together with the description, serves to explain the features, advantages, and principles of the invention. In the drawings:

FIG. 1 is a process flow diagram illustrating one embodiment of a method for extracting renewable materials from oleaginous microorganisms.

DETAILED DESCRIPTION

The invention provides methods and systems for extracting renewable materials from oleaginous microorganisms that desirably may result in a high yield of material extracted and minimal disruption of the cells and cell wall structures. The renewable materials can be used in biofuels production. Production of biofuels from microorganisms may have many advantages over production of biofuels from plants (including oilseeds), such as short life cycle, less labor requirement, independence of season and climate, and easier scale-up. Cultivation of microorganisms also does not require large acreages of farmland and there is less competition with food production.

As used herein, the term "renewable material" preferably refers to a substance and/or an item that has been at least partially derived from a source and/or a process capable of being replaced at least in part by natural ecological cycles and/or resources. Renewable materials may broadly include, for example, chemicals, chemical intermediates, solvents, adhesives, lubricants, monomers, oligomers, polymers, biofuels, biofuel intermediates, biogasoline, biogasoline blendstocks, biodiesel, green diesel, renewable diesel, biodiesel blend stocks, biodistillates, biochar, biocoke, biological oils, renewable building materials, and/or the like. As a more specific example, the renewable material may include, without being limited to, any one or more of the following: methane, ethanol, n-butanol, isobutanol, 2-butanol, fatty alcohols, isobutene, isoprenoids, triglycerides, lipids, fatty acids, lactic acid, acetic acid, propanediol, butanediol. According to certain embodiments, the renewable material may include one or more biofuel components. For example, the renewable material may include an alcohol, such as ethanol, butanol, or isobutanol, or lipids. In certain embodiments, the renewable material can be derived from a living organism, such as algae, bacteria, fungi, and/or the like. According to certain embodiments, the renewable material is a lipid, such as fatty acids with a carbon chain length profile at least somewhat similar to rapeseed oil.

The term "biofuel" preferably refers to components and/or streams suitable for use as a fuel and/or a combustion source derived at least in part from renewable sources. The biofuel can be sustainably produced and/or have reduced and/or no net carbon emissions (total carbon lifecycle) to the atmosphere, such as when compared to fossil fuels. According to certain embodiments, renewable sources can exclude materials mined or drilled, such as from the underground. In certain embodiments, renewable sources can include single cell organisms, multi-cell organisms, plants, fungi, bacteria, algae, cultivated crops, non-cultivated crops, timber, and/or the like.

According to certain embodiments, the renewable sources include microorganisms. Biofuels can be suitable for use as transportation fuels, such as for use in land vehicles, marine vehicles, aviation vehicles, and/or the like. More particularly, the biofuels may include gasoline, diesel, jet fuel, kerosene, and/or the like. Biofuels can be suitable for use in power generation, such as raising steam, exchanging energy with a suitable heat transfer media, generating syngas, generating hydrogen, making electricity, and/or the like. According to certain embodiments, the biofuel is a blend of biodiesel and petroleum diesel.

The term "biodiesel," as used herein, refers to components or streams suitable for direct use and/or blending into a diesel pool and/or a cetane supply derived from renewable sources. Suitable biodiesel molecules can include fatty acid esters, monoglycerides, diglycerides, triglycerides, lipids, fatty alcohols, alkanes, naphthas, distillate range materials, paraffinic materials, aromatic materials, aliphatic compounds (straight, branched, and/or cyclic), and/or the like. Biodiesel can be used in compression ignition engines, such as automotive diesel internal combustion engines, truck heavy duty diesel engines, and/or the like. In the alternative, the biodiesel can also be used in gas turbines, heaters, boilers, and/or the like. According to certain embodiments, the biodiesel and/or biodiesel blends meet or comply with industrially accepted fuel standards, such as B5, B7, B10, B15, B20, B40, B60, B80, B99.9, B100, and/or the like.

According to certain embodiments, a renewable diesel (hydrotreated) and/or renewable diesel blends meet or comply with industrially accepted fuel standards, such as B5, B7, B10, B15, B20, B40, B60, B80, B99.9, B100, and/or the like.

The term "lipid," as used herein, refers to oils, fats, waxes, greases, cholesterol, glycerides, steroids, phosphatides, cerebrosides, fatty acids, fatty acid related compounds, derived compounds, other oily substances, and/or the like. Lipids can be made in living cells and can have a relatively high carbon content and a relatively high hydrogen content with a relatively lower oxygen content. Lipids typically include a relatively high energy content, such as on a weight basis.

The term "organism," as used herein, refers to an at least relatively complex structure of interdependent and subordinate elements whose relations and/or properties can be largely determined by their function in the whole. The organism can include an individual designed to carry on the activities of life with organs separate in function but mutually dependent. Organisms can include a living being, such as capable of growth, reproduction, and/or the like. According to certain embodiments, microorganisms include single cell (unicellular), cell clusters, or multicellular relatively complex organisms.

The organism can include any suitable simple (mono) cell being, complex (multi) cell being, and/or the like. Organisms can include algae, fungi (including yeast), bacteria, and/or the like. The organism can include microorganisms, such as cyanobacteria, bacteria or protozoa. The organism can include one or more naturally occurring organisms, one or more genetically modified organisms, combinations of naturally occurring organisms and genetically modified organisms, and/or the like. Embodiments with combinations of multiple different organisms are within the scope of the disclosure. Any suitable combination or organism types or kinds can be used, such as one or more organism (yeast and bacteria, different genera, different species, or different variants), at least about two organism types, at least about five organism types, about two organism types to about twenty organism types, and/or the like.

In one embodiment, the organism can be a single cell member or the fungal kingdom, such as a yeast, for example. Examples of oleaginous yeast that can be used include, but are not limited to the following oleaginous yeasts: *Candida apicola, Candida* sp., *Cryptococcus curvatus, Cryptococcus terricolus, Debaromyces hansenii, Endomycopsis vernalis, Geotrichum carabidarum, Geotrichum cucujoidarum, Geotrichum histendarum, Geotrichum silvicola, Geotrichum vulgare, Hyphopichia burtonii, Lipomyces lipofer, Lypomyces orentalis, Lipomyces starkeyi, Lipomyces tetrasporous, Pichia mexicana, Rodosporidium sphaerocarpum, Rhodosporidium toruloides Rhodotorula aurantiaca, Rhodotorula dairenensis, Rhodotorula diffluens, Rhodotorula glutinus, Rhodotorula glutinis, Rhodotorula gracilis, Rhodotorula graminis, Rhodotorula minuta, Rhodotorula mucilaginosa, Rhodotorula mucilaginosa, Rhodotorula terpenoidalis, Rhodotorula toruloides, Sporobolomyces alborubescens, Starmerella bombicola, Torulaspora delbruekii, Torulaspora pretoriensis, Trichosporon behrend, Trichosporon brassicae, Trichosporon domesticum, Trichosporon laibachii, Trichosporon loubieri, Trichosporon loubieri, Trichosporon montevideense, Trichosporon pullulans, Trichosporon* sp., *Wickerhamomyces canadensis, Yarrowia lipolytica,* and *Zygoascus meyerae.*

The organism can operate, function, and/or live under any suitable conditions, such as anaerobically, aerobically, photosynthetically, heterotrophically, and/or the like. According to certain embodiments, the yeast may be cultured heterotrophically in the presence of air.

The term "oleaginous," as used herein, refers to oil bearing, oil containing and/or producing oils, lipids, fats, and/or other oil-like substances. Oleaginous may include organisms that produce at least about 20 percent by weight of oils, at least about 30 percent by weight of oils, at least about 40 percent by weight oils, at least about 50 percent by weight oils, at least about 60 percent by weight oils, at least about 70 percent by weight oils, at least about 80 percent by weight oils, and/or the like of the total weight of the organism. Oleaginous may refer to a microorganism during culturing, lipid accumulation, at harvest conditions, and/or the like.

Renewable materials can be extracted or separated from oleaginous microorganisms by changing the cell wall structure of the microorganism. A microorganism cell wall may contain small pores within the structure, such as for diffusion of cellular materials. With conditioning according to certain embodiments, these pores can be increased in number, size and/or permeability using a variety of techniques, described in detail below. The increase in the number, size and/or permeability of the pores within the cell wall of the microorganism allows for the extraction or removal of renewable material from within the internal structure of the microorganism. Compared to other methods of extracting renewable materials from microorganisms, the methods described herein may result in a higher yield of material extracted and/or minimal disruption of the cells and/or cell wall structures.

In general, renewable materials may be separated from microorganisms by conditioning cell walls of the microorganisms to form, open, and/or enlarge pores. Once the pores reach a sufficient state (such as are large enough to allow the renewable material or lipid to pass through), at least a portion of the renewable material may be removed from the microorganism through the pores and without rupture of the cell wall structure. A cell wall rupture includes a hole, tear or opening with a length or a diameter of at least about 50 percent of a diameter of the cell, according to certain embodiments. According to certain embodiments, cell wall at least substantially intact excludes lysed cells.

Conditioning the cell walls of the microorganisms to form, open, or enlarge pores may involve denaturing the cell wall structures and/or components. The cell wall structures and/or components may include, but are not limited to, transport proteins, integral membrane proteins, receptor proteins, agglutination proteins, antigenic proteins, septum, bud scars, decorating carbohydrates, non-structural carbohydrates, structural carbohydrates, glucans, mannans, mannoproteins, acetylglucosamine, chitin, dolipores, pore caps, protein cross-links, carbohydrate cross-links, protein-carbohydrate cross-links, embedded lipids, phospholipids, glycerides, sterols, sterol esters, and combinations thereof.

Treatment steps for conditioning the cell walls may include a thermal treatment, a chemical treatment, an enzymatic treatment, and/or a mechanical treatment. These treatment steps may involve suitable adjustments to temperature, steam popping, acid treatment, alkali treatment, solvent selection, and various other techniques. For instance, a thermal treatment may be carried out at a temperature of at least about 80 degrees Celsius. Any of these conditioning treatments may be carried out for a duration of at least about 10 minutes. Also, any of these conditioning treatments may be carried out in a pH range of about 2 to about 14.

As an example, a thermal treatment may be carried out at a temperature of about 120 degrees Celsius for about 4 hours. By conditioning the cell walls to increase the pore size, number of pores, and/or cell wall permeability, the material within the microorganism can diffuse through the modified cell wall structure to allow for the recovery of the renewable material. Furthermore, since the cell walls are merely modified and not destroyed, the cell itself may remain at least substantially intact.

Upon conditioning, the formed or enlarged pores may include macropores, mesopores and/or micropores. According to certain embodiments, mesopores have a diameter of about 2 nanometers to about 50 nanometers, while micropores have a diameter of less than about 2 nanometers, measured as zeolite surface area.

According to certain embodiments, the conditioned microorganism comprises pores with a mean pore diameter of at least about 4 nanometers, at least about 10 nanometers, at least about 20 nanometers, at least about 40 nanometers, at least about 50 nanometers, at least about 80 nanometers, about 4 nanometers, about 10 nanometers, about 20 nanometers, about 40 nanometers, about 4 nanometers to about 40 nanometers, about 6 nanometers to about 20 nanometers, or about 2 nanometers to about 10 nanometers.

According to certain embodiments, the mean pore diameter has a ratio to the mean cell diameter of the conditioned microorganism of at least about 0.01, at least about 0.05, at least about 0.1, about 0.2, about 0.01 to about 0.1, about 0.05 to about 0.1, or about 0.1.

According to certain embodiments, at least about 50 percent, at least about 60 percent, at least about 70 percent, at least about 80 percent, or at least about 90 percent, about 50 to about 90 percent, about 70 to about 90 percent, or about 80 to about 90 percent of total pores in the cell walls are mesopores after conditioning, based on overall number of pores.

According to certain embodiments, conditioned microorganisms may have a ratio of zeolite surface area:matrix surface area of greater than about 8, while a ratio of the zeolite surface area:matrix surface area of unconditioned microorganisms is about 2. For example, an oleaginous yeast may have a zeolite surface area:matrix surface area ratio of about 2 before conditioning and a zeolite surface area:matrix surface area ratio of about 8 after conditioning.

Microorganisms on which the processes herein may be carried out include, but are not limited to, algae, fungi, and bacteria. For example, a suitable fungi may include oleaginous yeast, such as those belonging to the genus *Rhodotorula*, *Pseudozyma*, or *Sporidiobolus*.

According to certain embodiments, the yeast belongs to the genus *Sporidiobolus pararoseus*. In a specific embodiment, the disclosed microorganism is the microorganism corresponding to ATCC Deposit No. PTA-12508 (Strain MK29404 (Dry1-13J)). In another specific embodiment, the microorganism is the microorganism corresponding to ATCC Deposit No. PTA-12509 (Strain MK29404 (Dry1-182J)). In another specific embodiment, the microorganism is the microorganism corresponding to ATCC Deposit No. PTA-12510 (Strain MK29404 (Dry1-173N)). In another specific embodiment, the microorganism is the microorganism corresponding to ATCC Deposit No. PTA-12511 (Strain MK29404 (Dry55)). In another specific embodiment, the microorganism is the microorganism corresponding to ATCC Deposit No. PTA-12512 (Strain MK29404 (Dry41)). In another specific embodiment, the microorganism is the microorganism corresponding to ATCC Deposit No. PTA-12513 (Strain MK29404 (Dry1)). In another specific embodiment, the microorganism is the microorganism corresponding to ATCC Deposit No. PTA-12515 (Strain MK29404 (Dry1-147D)). In another specific embodiment, the microorganism is the microorganism corresponding to ATCC Deposit No. PTA-12516 (Strain MK29404 (Dry1-72D)).

In other embodiments, the yeast belongs to the genus *Rhodotorula ingeniosa*. In a specific embodiment, the disclosed microorganism is the microorganism corresponding to ATCC Deposit No. PTA-12506 (Strain MK29794 (KDry16-1)). In another specific embodiment, the disclosed microorganism is the microorganism corresponding to ATCC Deposit No. PTA-12507 (Strain MK29794 (KDry7)). In another specific embodiment, the disclosed microorganism is the microorganism corresponding to ATCC. Deposit No. PTA-12514 (Strain MK29794 (K200 Dry1)). In another specific embodiment, the disclosed microorganism is the microorganism corresponding to ATCC Deposit No. PTA-12517 (Strain MK29794 (33 Dry1)).

The renewable material may be removed from the microorganism through the pores using any one or more of a variety of treatments including, but not limited to, aqueous extraction techniques (e.g. pH adjustment), solvent extraction techniques (e.g. polar or non-polar), and mechanical extraction techniques. One example of an extraction process resulting in increased pores or permeability is illustrated in FIG. 1. Examples of mechanical extraction techniques or mechanical treatments include extrusion, pressing, expelling, and the like. A mechanical disruption device, such as a homogenizer, a bead mill, a high-shear mixer, a press, an extruder, pressure disruption, wet milling, dry milling, or the like, may also be used to assist in removing the renewable material from the microorganism and resulting in cellular debris with cell walls at least substantially intact. According to certain embodiments, solvent extraction techniques may exclude use of a mechanical disruption device.

By conditioning the microorganism as described herein, the extraction yield of the conditioned microorganisms may be markedly improved over unconditioned microorganisms. According to certain embodiments, a microorganism that includes at least about 50 percent of the renewable material on a weight basis may have at least about 50 percent by weight of the renewable material pass through the pores as a result of the removal treatment. For example, an oleaginous yeast that includes at least about 50 weight percent lipids before extraction may have at least about 50 weight percent of the lipids removed through the pores. According to certain embodiments, the delipidated yeast may have less than about 20 weight percent of lipids remaining in the cell versus the unconditioned cell.

There are several techniques that can be used to measure the porosity and permeability of a microorganism, including: fluorescent dyes and flow cytometry (e.g. Fluorescein diacetate and ethidium bromide), measurement of microorganism sieving properties with external probing molecules (e.g. glycols and polyglycols), helium displacement and nitrogen adsorption of freeze dried microorganism, polycation assay (e.g. measure adsorbance of DEAE-Dextran at 260 nm), and HP gel filtration.

One metric used to characterize the performance of the described microorganisms is fatty acid extractability, or FAE. The FAE of any of the microorganisms according to the disclosure can be calculated according to the following formula:

$$\frac{\ell}{b \times C_{biomass}} = 1 - \left(\frac{c_{biomeal} \times (100 - C_{biomass})}{C_{biomass} \times (100 - c_{biomeal})}\right)$$

wherein b is the total biomass after the steps of conditioning and removing, typically measured in grams;

$C_{biomass}$ is the percentage of FAME prior to the steps of conditioning and removing, wherein $C_{biomass}$ is calculated as total grams FAME over total grams biomass; the term "FAME," as used herein, refers to a fatty acid methyl ester;

$c_{biomeal}$ is the percentage of FAME after the steps of conditioning and removing, wherein $c_{biomeal}$ is calculated as total grams FAME over total grams biomeal; and l is the total mass of oil after the steps of conditioning and removing, but prior to the oil recovery step, typically measured in grams.

According to certain embodiments, the methods described herein may result in an increase in the oil or fatty acid extractability index of the microorganism. For example, the method may result in an increase in the FAE index of the microorganism of at least about 10 weight percent. According to certain embodiments, the increase in FAE index may be at least about 20 weight percent, at least about 30 weight percent, or at least about 40 weight percent.

According to certain embodiments, following oil recovery with hexane, the mass of the oil is measured (L). Also measured is the FAME after oil recovery with hexane. In certain embodiments, vacuum evaporation, as is known in the art, is performed on the sample prior to FAME measurement.

The oil extraction yield of any of the microorganisms according to the disclosure can be calculated according to the following formula:

$$100 \times \frac{L \times C_{oil}}{B \times C_{biomass}}$$

wherein B is the total biomass prior to the steps of conditioning and removing, typically measured in grams;

$C_{biomass}$ is the percentage of FAME prior to the steps of conditioning and removing, wherein $C_{biomass}$ is calculated as total grams FAME over total grams biomass;

$C_{oil}$ is the percentage of FAME after the steps of conditioning and removing and oil recovery, wherein $C_{oil}$ is calculated by total grams FAME over total grams oil; and L is the total mass of oil after the steps of conditioning and removing and oil recovery, typically measured in grams. Obtaining these measurements from the microorganism or fermentation broth is within the ability of one of ordinary skill in the art.

According to certain embodiments, the methods described herein may result in an increase in the oil extraction yield of the microorganism. For example, the method may result in an increase in the oil extraction yield of the microorganism of at least about 10 weight percent. According to certain embodiments, the increase in oil extraction yield may be at least about 20 weight percent, at least about 30 weight percent, or at least about 40 weight percent.

The oil recovery index is the ratio of the oil extraction yield to the oil extractability. According to certain embodiments, the methods described herein may result in an increase in oil recovery index of at least about 10 weight percent. According to certain embodiments, the increase in oil recovery index may be at least about 20 weight percent, at least about 30 weight percent, or at least about 40 weight percent.

Through the conditioning of the cell walls and removal of renewable material through the pores, the cell walls may remain at least substantially intact. According to certain embodiments, at least about 10 percent, at least about 20 percent, at least about 30 percent, at least about 40 percent, at least about 50 percent, at least about 60 percent, at least about 70 percent, at least about 80 percent, at least about 90 percent, or at least about 95 percent of the cell walls remain at least substantially intact, on a number basis. According to certain embodiments, about 50 percent to about 80 percent of the cell walls remain intact on a number basis.

According to certain embodiments, following the conditioning and removal, the microorganism may end up with a final mesopore content of at least about 10 percent, at least about 20 percent, at least about 30 percent, at least about 40 percent, at least about 50 percent, at least about 60 percent, at least about 70 percent, at least about 80 percent, or at least about 90 percent of the total pores on a number basis. According to certain embodiments, the microorganism has a final mesopore content of about 50 percent to about 90 percent of the total pores.

The renewable materials as disclosed herein can be used for the manufacture of a food, supplement, cosmetic, or pharmaceutical composition for a non-human animal or human. Renewable materials can be manufactured into the following non-limiting examples: food products, pharmaceutical compositions, cosmetics, and industrial compositions. According to certain embodiments, the renewable material is a biofuel or biofuel precursor.

A food product is any food for animal or human consumption, and includes both solid and liquid compositions. A food product can be an additive to animal or human foods, and includes medical foods. Foods include, but are not limited to, common foods; liquid products, including milks, beverages, therapeutic drinks, and nutritional drinks; functional foods; supplements; nutraceuticals; infant formulas, including formulas for pre-mature infants; foods for pregnant or nursing women; foods for adults; geriatric foods; and animal foods. In certain embodiments, the microorganism, renewable material, or other biological product disclosed herein can be used directly as or included as an additive within one or more of: an oil, shortening, spread, other fatty ingredient, beverage, sauce, dairy-based or soy-based food (such as milk, yogurt, cheese and ice-cream), a baked good, a nutritional product, e.g., as a nutritional supplement (in capsule or tablet form), a vitamin supplement, a diet supplement, a powdered drink, a finished or semi-finished powdered food product, and combinations thereof.

As noted above, the renewable material may be a biofuel or biofuel precursor. More particularly, the renewable material may include lipids, organic acids, amino acids, alcohols, esters, alkanes, alkenes, olefins, paraffins, waxes, or any combination thereof. According to certain embodiments, the renewable material may include substantially polar materials, or substantially non-polar materials. According to certain embodiments, a partition, phase, or layer may separate polar renewable materials from non-polar renewable materials.

Methods for producing biofuels are also included herein. According to certain embodiments, a method for producing biofuels includes culturing yeast on sugar to accumulate lipids within cell walls of the yeast; conditioning the yeast to form or enlarge pores in the cell walls; removing the lipids through the pores in the cell walls; separating the lipids from the yeast; and converting the lipids into a biofuel. The lipids may be converted into a biofuel through the use of hydrotreating or transesterification, for example. A mixture for producing biofuels may include delipidated oleaginous microorganisms with cell walls substantially intact, and lipid material.

According to certain embodiments, the invention may be directed to a manufacturing facility for producing biofuels. According to certain embodiments, the manufacturing facility may include a lipid accumulation unit, and a lipid extraction unit in fluid communication with the lipid accumulation unit. The lipid extraction unit may include a cell conditioning device and a lipid separation device. The cell conditioning device may include one or more pieces of heat transfer equipment. The lipid separation device may include one or more pieces of extraction equipment.

According to certain embodiments, the invention may be directed to a delipidated microorganism, a renewable material, and/or a biofuel made according to any of the methods described herein.

Example 1

In this example, the microorganism MK 29404-Dry 1 was in a fermentation broth of sucrose-defined media. During the conditioning step, the fermentation broth was heated at 80° C. Far 3 hours prior to drum drying the broth containing the microorganism. During the removing step, the drum dried material was subsequently soaked in hexane at a ratio of between 1:5 and 1:12 (oil:hexane), without any mixing at room temperature, for between 30 minutes and 1 day. This resulted in an oil extractability of between 33 percent and 43 percent, determined by analyzing the residual biomass and determining the quantity of oil dissolved in the solvent. This material was viewed under a microscope and greater than 95 percent of the cells appeared to be intact, i.e. no cell rupture.

Example 2

In this example, the microorganism MK 29404-Dry 1 was in fermentation broth of sucrose-defined media. During the condition step, the broth containing the microorganism was processed through a bead mill at 380 ml/min three times (3 pass). During the removing step, a sample of the material was dried down (using a freeze dryer) and analyzed for oil extractability. The oil extractability, determined by washing the dry sample (3 g) with (30 ml) hexane and determining the fat content of the sample, resulted in an oil extractability of approximately 85 percent.

Example 3

In this example, the microorganism MK 29404-Dry 1 was in a fermentation broth of sucrose-defined media. During the conditioning step, the fermentation broth was heated at 80° C. for 1 hour prior to additional temperature pre-treatment. A temperature pre-treatment of a proportion (10 liters of the 80 liter fermentation broth) of the fermentation broth was undertaken at 121 degrees Celsius for 4 hours. During the removing step, a sample of the material was dried down (using a freeze dryer) and analyzed for oil extractability. The oil extractability, determined by washing the dry sample (3 g) with (30 ml) hexane and determining the fat content of the sample, of the pre-treated fermentation broth was >76 percent, which was an improvement over the sample in Example 1.

The pre-treated fermentation broth was then passed through a bead mill at a rate of 380 ml/min (1 pass) with the resulting sample having an oil extractability of >93 percent. As in Example 1, upon visual inspection, the cells appeared to be whole cells prior to processing through the bead mill.

The method in this Example is also an improvement over Example 2, as a higher oil extractability was achieved with less mechanical disruption, since the sample underwent 1 pass rather than 3 passes.

Example 4

In this example, three samples of pasteurized whole cell yeast biomass were conditioned and compared. Each sample was evacuated for many days before analysis, and each sample underwent four refinement steps. Argon was used (at 87.3 degrees Kelvin) for microporous analysis. Data is provided in Table 1, including the extractable oil (Ex. Oil), total specific surface area (TSA) in $m^2$/gm, matrix (mesopore) specific surface area (MSA) in $m^2$/gm, zeolite (micropore) specific surface area (ZSA) in m2/gm, zeolite surface area/matrix surface area ratio (Z/M), and zeolite surface area/total surface area ratio (Z/TSA), for each of the three samples.

TABLE 1

| | Post-Conditioning Biomass Evaluation | | | | | | |
|---|---|---|---|---|---|---|---|
| Treatment | Ex. Oil | TSA | MSA | ZSA | TPV | Z/M | Z/TSA |
| 1  80° C., 3 hours | 40% | 10.696 | 1.052 | 9.644 | 0.0067 | 9.17 | 0.90 |
| 2  121° C.; 4 hours | 54% | 9.11 | 0.672 | 8.429 | 0.0035 | 12.54 | 0.93 |
| 3  121° C., 4 hours | 85% | 14.249 | 0.72 | 13.53 | 0.0035 | 18.79 | 0.95 |

As shown in Table 1, in each case the zeolite surface area/matrix surface area ratio of the conditioned sample was above 8.

It will be apparent to those skilled in the art that various modifications and variations can be made in the disclosed structures and methods without departing from the scope or spirit of the invention. Particularly, descriptions of any one embodiment can be freely combined with descriptions or other embodiments to result in combinations and/or variations of two or more elements or limitations. Other embodiments of the invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. A process for separation of renewable materials from microorganisms, the process comprising:

conditioning cell walls of microorganisms containing a renewable material selected from the group consisting of methane, ethanol, n-butanol, isobutanol, 2-butanol, fatty alcohols, isobutene, isoprenoids, triglycerides, lipids, fatty acids, lactic acid, acetic acid, propanediol, butanediol, and combinations thereof, to form, open or enlarge pores without destroying the cell walls, wherein the conditioning comprises a treatment selected from the group consisting of thermal treatment, chemical treatment, enzymatic treatment, mechanical treatment, and combinations thereof; and removing at least a portion of the renewable material through the pores while the cell walls remain at least substantially intact without lysing the cell walls.

2. The process of claim 1, wherein the microorganism comprises oleaginous yeast.

3. The process of claim 2, wherein the oleaginous yeast belongs to the genus *Rhodotorula, Pseudozyma*, or *Sporidiobolus*.

4. The process claim 1, wherein the conditioning comprises a thermal treatment at about 120 degrees Celsius for about 4 hours.

5. The process of claim 1, wherein the removing comprises contact with a solvent or use of a mechanical disruption device comprising a homogenizer, a bead mill, a high-shear mixer, or any combination thereof.

6. The process of claim 1, wherein:

the microorganisms comprise at least about 20 percent of the renewable material on a weight basis; and at least about 50 percent of the renewable material passes through the pores during the step of removing on a weight percent basis.

7. The process of claim 1, wherein at least 50 percent of total pores comprise mesopores after conditioning, on a number basis.

8. The process of claim 2, wherein the oleaginous yeast comprises at least about 50 weight percent lipids before extraction.

9. The process of claim 2, wherein the removing comprises removing at least about 50 weight percent of the lipids from the oleaginous yeast.

10. The process of claim 2, wherein at least about 70 percent of total pores formed are mesopores, on a number basis.

11. The process of claim 2, wherein the conditioning comprises a thermal treatment that comprises temperatures above about 80 degrees Celsius, times for at least about 10 minutes, and a pH range of about 2 to about 14.

* * * * *